United States Patent [19]

Bodor

[11] Patent Number: 4,496,570

[45] Date of Patent: Jan. 29, 1985

[54] 4,5αEPOXYMORPHINAN-6-SPIRO-2'-(4'-CARBOXY,1',3'-THIAZOLIDINE)DERIVATIVES

[75] Inventor: Nicholas S. Bodor, Gainesville, Fla.

[73] Assignee: Key Pharmaceuticals, Inc., Miami, Fla.

[21] Appl. No.: 477,447

[22] Filed: Mar. 21, 1983

[51] Int. Cl.³ ............... C07D 489/08; A61K 31/485
[52] U.S. Cl. .................................. 514/282; 546/15; 544/125; 514/231
[58] Field of Search ............ 546/15; 424/260, 248.51; 544/125

[56] References Cited

U.S. PATENT DOCUMENTS 2,619,485 11/1952 Chabrier et al. .................... 544/125
4,362,870 12/1982 Portoghese ......................... 542/403

FOREIGN PATENT DOCUMENTS 981046 1/1965 United Kingdom ................. 546/15

OTHER PUBLICATIONS

Hazum et al., *Biochemical and Biophysical Research Communications*, vol. 104, pp. 347–353, (01/15/82).
British Drug Houses, Ltd., Chemical Abstracts, vol. 61, 4365e–4366d, (1964).

*Primary Examiner*—Donald G. Daus
*Assistant Examiner*—Diana G. Rivers
*Attorney, Agent, or Firm*—Wegner & Bretschneider

[57] ABSTRACT

Compounds the structural formula

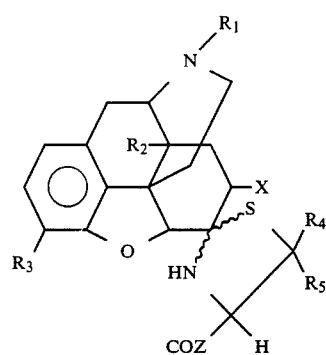

or their pharmaceutically acceptable salts, wherein X is H or $CH_3$, Z is $NH_2$ or $OR_6$, $R_1$ is a $C_{1-8}$ alkyl, $C_{3-6}$-cycloalkylmethyl, or phenyl-$C_{1-2}$alkyl group, $R_2$ is hydrogen, hydroxy, chloro or fluoro, $R_3$ is hydrogen, hydroxy, methoxy, —OCO—($C_{1-6}$-alkyl) or morpholinoethoxy, $R_4$ and $R_5$ may be the same or different and are H or $C_{1-6}$alkyl, $R_6$ is H, $C_{1-4}$ alkyl, $C_{3-5}$ alkenyl, $C_{3-7}$ cycloalkyl phenyl, or phenyl substituted by one to three alkyl groups with a total of 4 carbon atoms are useful opiod antagonists.

12 Claims, No Drawings

4,5α-EPOXYMORPHINAN-6-SPIRO-2'-(4'-CARBOXY,1',3'-THIAZOLIDINE)DERIVATIVES

The present invention relates to novel narcotic antagonists having a 6-spiro thiazolidine ring. More particularly, the invention relates to 4,5α-epoxymorphinan-6-spiro-2'-(4'carboxy-1'-3'-thiazolidine) derivatives of the structural formula

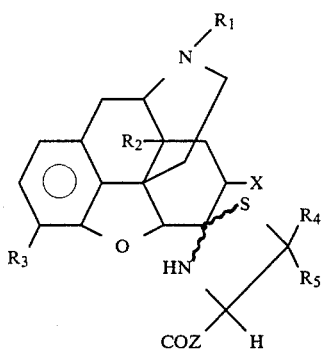

and pharmaceutically acceptable acid addition salts thereof.

In that formula $R_1$ can represent a $C_{1-8}$ alkyl, $C_{3-6}$ alkenyl, $C_{3-6}$cycloalkylmethyl, or phenyl-$C_{1-2}$alkyl group.

The radical $R_2$ is hydrogen, hydroxy, chloro or fluoro. $R_3$ is hydrogen, hydroxy, methoxy, —OCO—(-lower alkyl) or morpholinoethoxy.

$R_4$ and $R_5$ may be the same or different and are hydrogen or a lower lower alkyl of 1–6 carbon atom.

X is hydrogen or methyl.

Z is $OR_6$ or $NH_2$ and $R_6$ is hydrogen, $C_{1-4}$alkyl, $C_{3-5}$alkenyl, $C_{3-7}$-cycloalkyl, phenyl, or phenyl substituted by one to three alkyl groups, the alkyl groups having a total of 4 carbon atoms.

Among the lower alkyl groups which $R_6$ can represent are methyl, ethyl, straight chain and branched propyl and butyl.

$R_4$ and $R_5$ can be alkyl of the same type and straight chain and branched amyl and hexyl. The $C_{1-6}$-alkyl group in the carboxyloxyalkyl group, which $R_3$ can represent, is of the same type as described for $R_4$. $R_1$ can also be an alkyl group of the type described for $R_4$ and, in addition, a straight chain or branched heptyl or octyl.

The alkenyl groups referred to hereinabove include propenyl, butenyl, methylbutenyl, pentenyl and hexenyl groups. The $C_{3-6}$-cycloalkyl radicals referred to in the definition of the cycloalkyl-methyl group which $R_1$ can represent include cyclopropyl, cyclobutyl, cyclopentyl, cyclohexyl, methylcyclopentyl and the like. $R_6$ can represent the same type of cycloalkyl radical and such 7 carbon radicals as cycloheptyl and methylcyclohexyl. $R_1$ can represent a phenyl-$C_{1-2}$alkyl group as phenylmethyl, 1-phenethyl and 2-phenethyl.

$R_6$ can also represent an alkylated phenyl radical such as tolyl, xylyl, cumyl, diethylphenyl, and the like.

The pharmaceutically acceptable salts referred to above include such inorganic acid salts as the hydrochloride, hydrobromide, sulfate, nitrate and phosphate and such organic acid salts as the acetate, tartrate, citrate, fumurate, maleate, toluenesulfonate, and methanesulfonate.

In the case where $R_6$ is hydrogen, the compound can form metal salts and salts with organic bases.

The 4,5α-epoxymorphinan-6-spiro-2'-(4'-carboxy-1',3'-thiazolidine) ester compounds of this invention are prepared by contacting the correspondingly substituted morphinan-6-one with a cysteine derivative of the formula

$$R_6O—CO—CH(NH_2)—CR_4R_5—SH.$$

The free acid, in which $R_6$ is hydrogen, is obtained by conventional hydrolytic desterification of the corresponding alkyl phenyl ester or by hydrogenolysis of a benzyl ester 4'-carboxamides and peptides are obtained by substituting the corresponding cysteine or peptides for the esters. Thus the 6-oxomorphinan is agitated with a compound of the formula

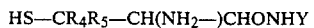
$$HS—CR_4R_5—CH(NH_2—)CHONHY$$

Y being H or α—$XH_2COO$(lower alkyl) group to yield the

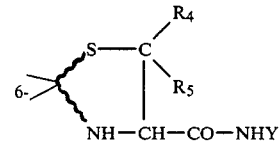

In the condensation of the cysteine derivative and the morphinan-6-one, there is an initial condensation reaction of the 6-oxo group with the amine group of the cysteine derivate. In the subsequent cyclization to form the thiazolidine ring, beta-attack predominates over alpha-attack, but both isomers are formed, as indicated by the wavy line in the generic structural Formula I.

The compounds of this invention are potent opioid antagonists of the same qualitative action as the parent opioids lacking the 6-spiro group. They were designed to produce a stronger, but reversible binding to the receptors, by forming an —S—S-type intermediate with sulfhydryl group of the receptor. The intermediate may be depicted by the formula:

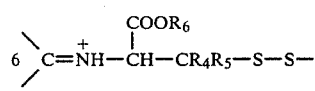

The compounds of this invention can be administered by the method employed with the analogous opioid agonists and antagonists lacking the 6-spiro substituents. The dosage can be reduced because of the greater effectiveness as illustrated in Example VII.

The following examples will further illustrate the invention, however, they are not to be construed as limiting that invention in spirit or in scope.

EXAMPLE I

Preparation of 17-allyl-4,5α-epoxy-3,14-dihydroxymorphinan-6-spiro-2'-(4'-carboethoxy-1',3'-thiazolidine dihydrochloride A mixture of 4 mmol of 17-allyl-4,5α-epoxy-3,14-dihydroxymorphinan-6-one hydrochloride (naloxone hydrochloride 1.46 g) and of 8 mmol cysteine ethyl ester hydrochloride (1.5 g) in 45 ml of dry pyridine is stirred at room temperature for 20 hours under a nitrogen atmosphere. The solution is concentrated in vacuo. The resulting mixture is partitioned between water (50 ml) and chloroform (50 ml). The pH of the aqueous layer is adjusted to 7.0 with 10% NaOH. After shaking, the organic layer is separated. The aqueous layer obtained is extracted twice with 50 ml of chloroform. The organic layers are combined, washed once with water, dried over sodium sulfate and evaporated to give a colorless oil. The oil is purified on a chromatographic column [neutral silica gel (silicAR CC-7), 100 g] using a mobile phase of a mixed solvent of chloroform and methanol (50:1). The selected fractions are collected and evaporated in vacuo to give a colorless oil. The oil is dissolved in 30 ml dry ethyl ether (30 ml) and excess hydrogen chloride in dry ethanol is added. The colorless powder obtained is filtered and dried over phosphorus pentoxide to give 6-spirothiazolidine dihydrochloride of naloxone as an amorphous powder; m.p. 171°–175° C. (dec). Elemental analysis for $C_{24}H_{30}N_2O_5S \cdot 2HCl \cdot 2H_2O$ calcd.: C, 50.79; H, 6.39; N, 4.94; S, 5,65; Cl, 12.49. Found: C, 50.55; H, 6.26; N, 4.97; S, 5.74; Cl, 12.56. IR (KBr) cm$^{-1}$: 1750, 1650, 1640, 1630, 1620, 1510, 1470, 1460, 1375, 1320, 1230, 1120, 1030, 950 and 900. NMR (DMSO-d$_6$) δ 1.0–4.0 (m), 4.24 (2H, q, J=Hz, —COOCH$_2$), 4.72 (1H, t, J-8 Hz, 4'-H), 5.02 and 5.14 ($\frac{1}{3}$H and $\frac{2}{3}$H, respectively, each s, 5-H), 5.2–6.0 (m), 6.6–6.9 (2H, m, aromatic protons).

EXAMPLE II

Preparation of 17-cyclopropylmethyl-4,5α-epoxy-3,14-dihydroxymorphinan-6-spiro-2'-(4'-carboethoxy-1',3'-thiazolidine) dihydrochloride A mixture of 2 mmol of 17-cyclopropylmethyl-4,5α-epoxy-3,14-dihydroxymorphinan-6-on (naltrexone 682 mg), with (4 mmol) of cysteine ethyl ester hydrochloride in 10 ml of dry pyridine is stirred at room temperature for 29 hrs under a nitrogen atmosphere. The solution is then concentrated in vacuo to give an oil which is partitioned between water (50 ml) and ethyl acetate (50 ml). The pH of the aqueous layer is adjusted to 7.0 with 10% sodium hydroxide. After shaking, the organic layer is separated. The aqueous layer obtained is further extracted twice with 50 ml portions of ethyl acetate. The combined organic layers are washed once with water, dried over sodium sulfate and evaporated to give a colorless oil. The oil is purified by column chromatography on neutral silica gel (silicAR CC-7, 70 g) using a mixed solvent of chloroform and methanol (100:1 20:1) as an eluant. The desired fractions are collected and evaporated to give the free base of the desired 6-spirothiazolidine. The free base obtained is converted to the dihydrochloride salt in the same way as described before. Thus, spirothiazolidine dihydrochloride of naltrexone is obtained as an amporphous powder, m.p. 175°–170° C. (dec.). Elemental analysis for $C_{25}H_{32}N_2O_5S \cdot 5HCl \cdot \frac{1}{2}H_2O$ calcd: C, 54.15; H, 6.36; N, 5.05; S, 5.78. Found: C, 54.18; H, 6.32; M. 5.09; S, 5.72/ IR (KBr) cm$^{-1}$: 1755, 1650, 1640 (sh), 1630, 1510, 1475, 1460, 1380, 1320, 1240, 1125, 1040, 950 and 905. NMR (DMSO-d$_6$) 0.3–4.0 (m), 4.24 (2H, q, J=7 Hz, —COOCH$_2$), 4.73 (1H, t, J-8.5 Hz, 4'-H), 5.02 and 5.15 ($\frac{1}{3}$H and $\frac{2}{3}$H, respectively, each S, 5-H), 6.5.6.9 (2H, m, aromatic protons).

EXAMPLE III

Preparation of 17-dimethallyl-4,5α-epoxy-3,14-dihydroxymorphinan-6-spiro-2'-(4'-carboethoxy-1',3'-thiazolidine)

A mixture of 2 mmol of 17-dimethallyl-4,5α-epoxy-3,14-dihydroxymorphinan-6-one hydrochloride and 4 mmol of cysteine ethyl ester hydrochloride in 25 ml of dry pyridine is agitated at room temperature for 24 hours under nitrogen. The solution is vacuum concentrated and the resulting mixture is partitioned between equal parts of water and chloroform. The aqueous layer is separated and neutralized by addition of 10% sodium hydroxide. After shaking, the organic layer is removed and the aqueous layer extracted repeatedly with chloroform. The combined organic extract is washed with water and dried over anhydrous sodium sulfate. The product is purified as in Example 1.

Substitution of an equimolar amount of the cysteine methyl ester, cyclopropyl ester, cyclobutyl ester, allyl ester, phenyl ester, and tolyl ester for the ethyl ester gives the corresponding methyl, cyclopropyl, cyclobutyl, allyl, phenyl and tolyl esters of 17-dimethylallyl-4,5α-epoxy-3,14-dihydroxymorphinan-6-spiro-2'-(4'-carboxy-1',3'-thiazolidine).

EXAMPLE IV

Preparation of 17-methyl-4,5α-epoxy-3-methoxymorphinan-6-spiro-2'-(4'-carbomethoxy-1',3'-thiazolidine)

A mixture of 3 mmol dihydrocodeninone hydrochloride and 6 mmol of cysteine methyl ester hydrochloride in 30 ml of anhydrous pyridene is agitated at room temperature for 18 hours in a nitrogen atmosphere. The solution is then concentrated under vacuum and the residue is partitioned between equal volumes of water and chloroform. The aqueous solution is neutralized with aqueous sodium hydroxide and, after agitation, the organic layer is separated and then extracted repeatedly with chloroform. The combined organic extracts are washed with water, dried over sodium sulfate and evaporated.

17-methyl-4,5α-epoxy-3-hydroxymorphinan-6-spiro-2'-(4-carbomethoxy-1',3'-thiazolidine) is obtained by substituting in the foregoing procedure 3 mmol of hydromorphone.

EXAMPLE V

Peparation of 17-cyclopropylmethyl-4,5α-epoxy-3,14-dihydroxymorphinan-6-spiro-2'-(4'-carboxy-5',5'-dimethyl-1',3'thiazolidine) esters A mixture of 1 mmol of naltrexone and 2 mmol of penicillamine ethyl ester hydrochloride in 7 ml of dried pyridine is stirred under a nitrogen atmosphere at room temperature for 36 hours. The solution is then concentrated under vacuum and the residual oil is partitioned between water and ethyl acetate. The aqueous layer is then neutralized with aqueous sodium hydroxide and, after shaking, the aqueous layer is separated and further extracted repeatedly with ethyl acetate. The combined organic solutions are washed once with water, dried over sodium sulfate and evaporated.

By the same procedure, condensation with the cyclopropylester, the cyclobutylester, the allyl ester, phenylester, the p-tolyl ester of penicillamine is carried out.

EXAMPLE VI

4,5-epoxy 3-hydroxy-5,17-dimethylmorphinan-6-spiro-2'-(4'-carboxy-1',3'-thiazolidine) esters and amides A mixture of 1 mmol of 4,5-epoxy-3-hydroxy-5,17-dimethylmorphinan-6-one (metopon) hydrochloride and 2 mmol of cysteine methyl ester hydrochloride in 15 ml pyridine is stirred at room temperature for 25 hours and then concentrated under vacuum and then partitioned between equal volumes of water and chloroform. The aqueous solution is neutralized with sodium hydroxide and extracted with chloroform. The chloroform extracts are combined, washed with water, dried over sodium sulfate and evaporated to produce 4,5-epoxy-3-hydroxy-5,17-dimethylmorphinan-6-spiro 2'-(4'-carbomethoxy-1',3'-thiazolidine).

Substitution of 2 mmol of cysteine amide in the above condensation produces the 4,5-epoxy-3-hydroxy-5,17-dimethylmorphinan-6-spiro-2'-(4'-carboxamido-1',3'-thiazolidine).

EXAMPLE VII

Antagonist activity of 17-allyl-4,5α-epoxy-3,14-dihydroxymorphinan-6-spiro-2'-(4'-carboethoxy-1',3'-thiazolidine) dihydrochloride (ST-N)

The potency of ST-N to block the depressant action of morphine on the guinea pig isolated ileum was determined. The depressant action of morphine was assessed on the contraction of longitudinal ileum muscle induced by co-axial electrical stimulation. For this, the terminal portion of ileum was quickly taken from a guinea pig killed by inhalation of $CO_2$. Segments of ileum were secured at one end over an electrode wire embedded in a glass tissue holder and placed in a tissue bath. The other end was attached to a force transducer (Grass FT. 03). Krebs solution (25 ml), bubbled with 95% $O_2$ at 37° C., covered the ileal segments. The initial resting tension on these segments was 1 g. Coaxial electrical stimulation was given at 1.5 times maximum as rectangular pulses of 0.5 msec duration at a frequency of 6-7/min. The twitch-like contractions were recorded on a Grass polygraph.

The segments of ileum were first exposed to morphine in graded concentrations for 1 to 3 minutes, until inhibition was maximal, and then washed with fresh Krebs solution allowing 20 minutes between each morphine application. Results were plotted as the percentage by which the size of the control twitch was reduced by each concentration of morphine. Morphine produced a concentration-related inhibition of the electrically-induced twitch contraction of ileal segments. ST-N shifted the morphine-response curve to the right in a parallel and concentration-related manner, demonstrating blocking of the effect of morphine.

Concentration-ratios were derived by dividing the concentration of morphine needed to produce a 50% inhibition of twitch contraction in the presence of each concentration of either Naloxone or ST-N ($A_B$) by the concentration of morphine producing a 50% depression of contraction in the absence of antagonist ($A_O$). These data were used to compare the potencies of Naloxone and ST-N by plotting the $\log_{10}$ of ($A_B/A_O - 1$) against the negative $\log_{10}$ of antagonist concentration. The lines of best fit among these points, as determined by the least squares method, intersect the abscissa at a concentration of antagonist which causes a two-fold blockade. The pA2 determined for Naloxone was 8.77. The pA2 value calculated for ST-N is 10.04, indicating that ST-N is about 22 times more potent than Naloxone in this system. The slopes of both lines are the same.

An additional comparison between ST-N and naloxone was carried out by subcutaneous administration in rats and determining water and food intake. Again ST-N showed a strong effect at very low dose levels of 0.78 mg/ml, evidencing a higher level of potency than naloxone.

What is claimed is:

1. A compound of the structural formula

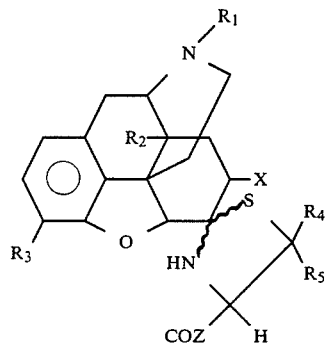

or its pharmaceutically acceptable salts, wherein
X is H or $CH_3$,
Z is $NH_2$ or $OR_6$,
$R_1$ is a $C_{3-6}$-alkenyl or $C_{3-6}$-cycloalkylmethyl,
$R_2$ is hydroxy, chloro or fluoro,
$R_3$ is hydrogen hydroxy, or —OCO—($C_{1-6}$-alkyl),
$R_4$ and $R_5$ may be the same or different and are H or $C_{1-6}$ alkyl,
$R_6$ is $C_{1-4}$ alkyl.

2. A compound according to claim 1 wherein
X is H
$R_1$ is a $C_{3-6}$ alkenyl,
$R_2$ and $R_3$ are hydroxy
$R_4$ and $R_5$ are hydrogen
and Z is $OR_6$.

3. A compound according to claim 2 which is 17-allyl-4,5α-epoxy-3,14-dihydroxymorphinan-6-spiro-2'-(4'-carboethoxy-1',3'-thiazolidine).

4. A compound according to claim 1 wherein $R_1$ is $C_{3-6}$-cycloalkylmethyl, $R_2$ and $R_3$ are hydroxy, $R_4$ and $R_5$ are hydrogen and Z is $OR_6$.

5. A compound according to claim 4 wherein $R_1$ is cyclopropylmethyl.

6. A compound according to claim 4 which is 17-cyclopropylmethyl-4,5α-epoxy-3-14-dihydroxymorphinan-6-spiro-2'-(4'-carboethoxy-1',3'-thiazolidine).

7. An opioid antagonist composition which comprises a dose, effective for producing antagonism to the depressant effect of an opioid, of a compound of the structural formula

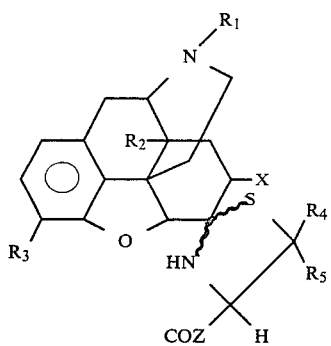

or its pharmaceutically acceptable salts, wherein
X is H or CH₃,
Z is NH₂ or OR₆,
R₁ is a C₃₋₆-alkenyl or
  C₃₋₆-cycloalkylmethyl,
R₂ is hydroxy, chloro or fluoro,
R₃ is hydrogen hydroxy, or —OCO—(C₁₋₆-alkyl),
R₄ and R₅ may be the same or different and are H or
  C₁₋₆ alkyl,
R₆ is C₁₋₄ alkyl.

8. A composition of claim 7 wherein the compound is 17-allyl-4,5α-epoxy-3,14-dihydroxymorphinan-6-spiro-2'-(4'-carboethoxy-1',3'-thiazolidine).

9. A composition according to claim 7 wherein the compound is 17 cylopropylmethyl-4,5α-epoxy-3,14-dihydroxymorphinan-6-spiro-2'-(4'-carbethoxy-1',3'-thiazolidine).

10. Method of producing antagonism to the depressant action of an opioid drug in a mammal in which there is administered to said mammal an effective antagonist dose of a compound of the structural formula

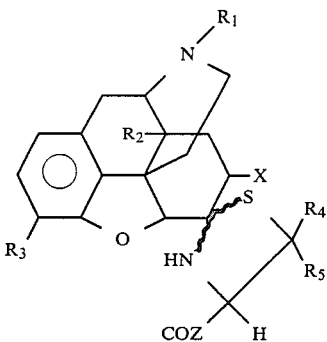

or its pharmaceutically acceptable salts, wherein
X is H or CH₃,
Z is NH₂ or OR₆,
R₁ is a C₃₋₆-alkenyl or
  C₃₋₆ cycloalkylmethyl,
R₂ is hydroxy, chloro or fluoro,
R₃ is hydrogen hydroxy, or —OCO—(C₁₋₆-alkyl),
R₄ and R₅ may be the same or different and are H or
  C₁₋₆ alkyl,
R₆ is C₁₋₄ alkyl.

11. Method according to claim 10, wherein the compound is 17-allyl-4,5α-epoxy-3,14-dihydroxymorphinan-6-spiro-2'-(4'-carboethoxy-1',3'-thiazolidine).

12. Method according to claim 10, wherein the compound is 17-cyclopropylmethyl-4,5α-epoxy-3,14-dihydroxymorphinan-6-spiro-2'-(4'-carbethoxy-1',3'-thiazolidine).

* * * * *